United States Patent [19]

Buckley

[11] Patent Number: 5,571,968
[45] Date of Patent: Nov. 5, 1996

[54] APPARATUS FOR MOUNTING A PLURALITY OF ULTRASONIC PROBES FOR MOVEMENT IN SPECIFIED DIRECTIONS FOR DETECTING DEFECTS IN A BODY

[75] Inventor: Paul S. Buckley, Derby, England

[73] Assignee: Rolls-Royce and Associates, Limited, Derby, England

[21] Appl. No.: 91,257

[22] Filed: Jul. 15, 1993

[30] Foreign Application Priority Data

Jul. 18, 1992 [GB] United Kingdom .................... 9215346

[51] Int. Cl.⁶ .................................................. G01N 29/04
[52] U.S. Cl. ............................... 73/623; 73/639; 376/249
[58] Field of Search ........................... 73/623, 637, 639, 73/640, 632; 376/249; 901/17; 976/DIG. 212

[56] References Cited

U.S. PATENT DOCUMENTS

| | | | |
|---|---|---|---|
| 3,888,362 | 6/1975 | Fletcher | 901/17 |
| 4,474,064 | 10/1984 | Naruse | 73/640 |
| 4,612,808 | 9/1986 | McKirdy | 73/639 |
| 4,672,852 | 6/1987 | Gugel et al. | 73/622 |

FOREIGN PATENT DOCUMENTS

| | | |
|---|---|---|
| 0025213 | 3/1981 | European Pat. Off. . |
| 1595826 | 6/1970 | France . |
| 3508415 | 9/1986 | Germany . |
| 78105293 | 6/1990 | Taiwan . |
| 1507272 | 12/1978 | United Kingdom . |

*Primary Examiner*—Hezron E. Williams
*Assistant Examiner*—Christine K. Oda
*Attorney, Agent, or Firm*—Cushman Darby & Cushman, L.L.P.

[57] ABSTRACT

An apparatus for detecting defects comprises a pair of ultrasonic probes which are gimballed onto a pair of elongate members. A pair of yokes are gimballed onto the elongate members. Springs cause an interaction between the yokes and the ultrasonic probes such that the ultrasonic beams travel in a plane parallel to the longitudinal direction of the elongate members. The elongate members are slidably mounted on a carriage and the elongate members are arranged apart at a predetermined angle. The carriage is mounted to travel on an arcuate member to scan the corner of joint between a pressure vessel and a nozzle in a direction radially with respect to the axis of the nozzle. The arcuate member is rotatably mounted to a support member to scan the corner or the joint circumferentially with respect to the axis of the nozzle.

22 Claims, 4 Drawing Sheets

APPARATUS FOR MOUNTING A PLURALITY OF ULTRASONIC PROBES FOR MOVEMENT IN SPECIFIED DIRECTIONS FOR DETECTING DEFECTS IN A BODY

FIELD OF THE INVENTION

The present invention relates to an apparatus for detecting defects in a wall of a hollow object, the wall having a contoured exterior surface. The present invention is particularly concerned with detecting defects in the weld joint between an inlet, or outlet, nozzle and a nuclear reactor pressure vessel using ultrasonic probes.

BACKGROUND OF THE INVENTION

The inspection of components, or objects, for defects using an ultrasonic time of flight technique is well known. In this technique two ultrasonic probes are used, with one ultrasonic probe located either side of the defect. The ultrasonic time of flight technique has the capability of detecting defects in the inner blend radius region and outer blend radius region of the welded interconnection between the inlet, or outlet, nozzle and the nuclear reactor pressure vessel.

The welded interconnection between the inlet, or outlet, nozzle and the nuclear reactor pressure vessel is not a uniform, or regular, geometric shape. This interconnection is an interconnection between a large diameter vertical cylinder, the nuclear reactor pressure vessel, and a small diameter horizontal cylinder, the inlet or outlet nozzle. The interconnection produces a saddle shaped corner, or bend, wherein the angle of the bend can vary from 90° to approximately 130° dependent upon the radial displacement about the axis of the small diameter horizontal cylinder.

However, practical implementation of the ultrasonic time of flight technique for use in detecting defects in weld joints between inlet, or outlet, nozzles and the nuclear reactor pressure vessel is difficult and costly. This is due to the fact that large numbers of beam angles and/or extremely complex probe array and scanning patterns are required to inspect the complex geometry of this interconnection.

SUMMARY OF THE INVENTION

The present invention seeks to provide an apparatus for detecting defects which reduces or overcomes the above mentioned problems.

Accordingly the present invention provides an apparatus for detecting defects in a wall of a hollow object, the object having a contoured exterior surface, the apparatus comprising a first ultrasonic probe pivotally mounted to a first member about a first axis, the first member is pivotally mounted to a first elongate member about a second axis, the first and second axes are mutually perpendicular and are arranged in a first plane, a second member pivotally mounted to a third member about a third axis, the third member is pivotally mounted to the first elongate member about a fourth axis, the third and fourth axes are mutually perpendicular and are arranged in a second plane, the second and fourth axes are spaced apart and are parallel, the second member is arranged to act on the first ultrasonic probe such that in operation the first ultrasonic probe transmits ultrasound into the object in a plane parallel to the first elongate member, a second ultrasonic probe pivotally mounted to a fourth member about a fifth axis, the fourth member is pivotally mounted to a second elongate member about a sixth axis, the fifth and sixth axes are mutually perpendicular and are arranged in a third plane, a fifth member pivotally mounted to a sixth member about a seventh axis, the sixth member is pivotally mounted to the second elongate member about an eighth axis, the seventh and eighth axes are mutually perpendicular and are arranged in a fourth plane, the sixth and eighth axes are spaced apart and are parallel, the fifth member is arranged to act on the second ultrasonic probe such that in operation the second ultrasonic probe receives ultrasound travelling in the object in a plane parallel to the second elongate member, the first and second elongate members are arranged at a predetermined angle such that the first ultrasonic probe and second ultrasonic probe are focused at a common point on the contoured exterior surface of the object.

The present invention also provides an apparatus for detecting defects in a wall of a hollow object, the object having a contoured exterior surface, the apparatus comprising a first ultrasonic probe pivotally mounted to a first member about a first axis, the first member is pivotally mounted to a first elongate member about a second axis, the first and second axes are mutually perpendicular and are arranged in first plane, a second member pivotally mounted to a third member about a third axis, the third member is pivotally mounted to the first elongate member about a fourth axis, the third and fourth axes are mutually perpendicular and are arranged in a second plane, the second and fourth axes are spaced apart and are parallel, the second member is arranged to act on the first ultrasonic probe such that in operation the first ultrasonic probe transmits ultrasound into the object in a plane parallel to the first elongate member.

The present invention will be more fully described, by way of example, with reference to the accompanying drawings in which:

DETAILED DESCRIPTION OF THE INVENTION

Figure 1:
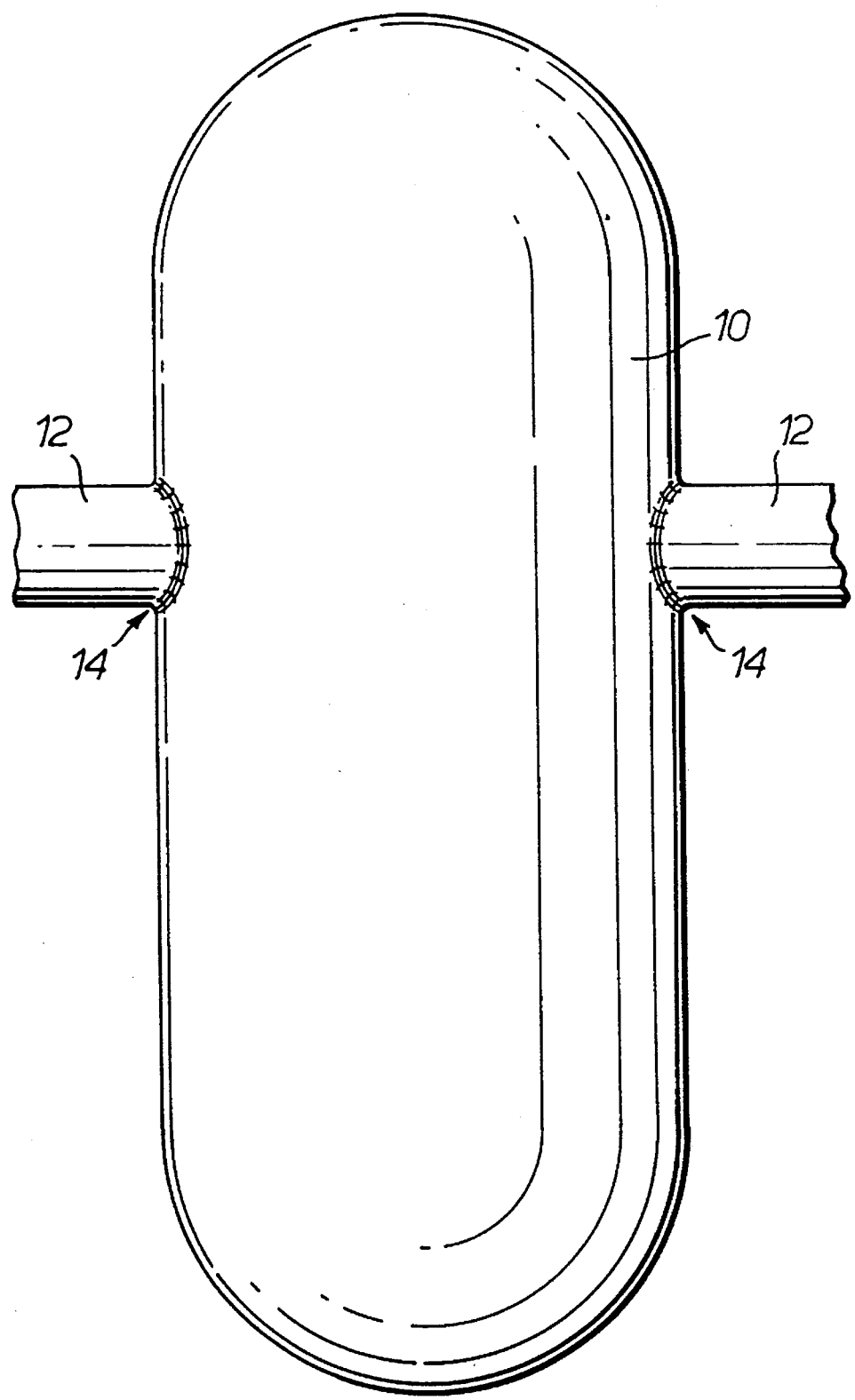
FIG. 1 is a view of a nuclear reactor pressure vessel showing inlet and outlet nozzles.
Figure 2:
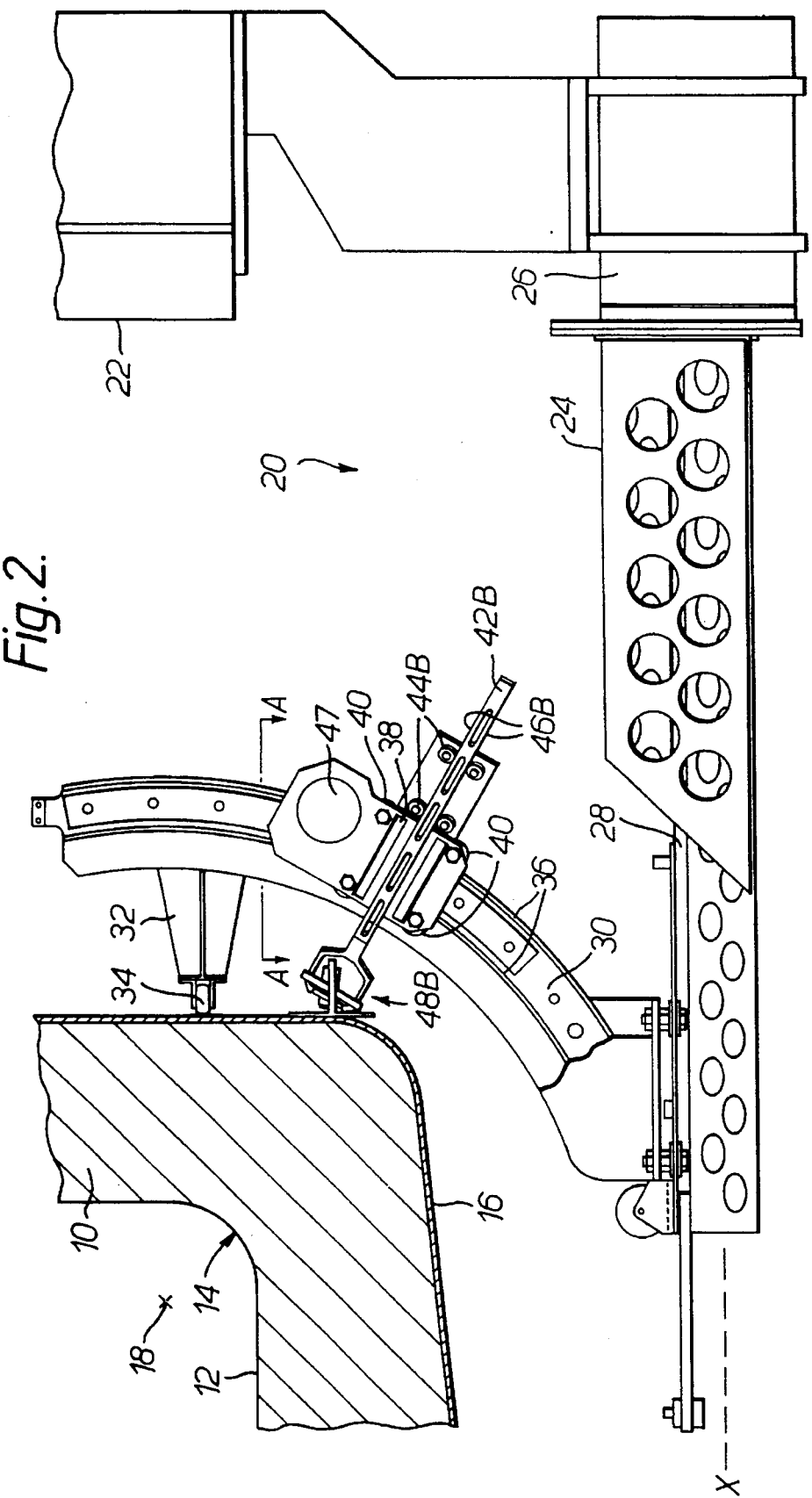
FIG. 2 is a partial side view in the plane of a nozzle and pressure vessel axes showing the apparatus according to the present invention.

FIG. 1 shows a view of a nuclear reactor pressure vessel 10 and its associated inlet and outlet nozzles 12. The corner, or bend, 14 interconnections between the inlet and outlet nozzles 12 and the pressure vessel 10 are also shown. These corner 14 interconnections vary between an angle of 90°, as shown in FIG. 2 for the regions of the corner 14 in a vertical plane containing the pressure vessel axis and the inlet, or outlet, nozzle 12 axis X and 110° to 130° for the regions of the corner 14 in a horizontal plane containing the axis X of the inlet, or outlet, nozzle The pressure vessel 10 has an inner cladding 16 of suitable material, for example stainless steel to provide resistance to radiation and corrosion.

The apparatus 20, as shown in FIGS. 2 to 5, for detecting defects for example cracks, comprises a mast which is supported at the top of the nuclear reactor pressure vessel 10 and extends vertically downwardly into the pressure vessel 10. The mast 22 supports a horizontal member 24 and the mast 22 has a motor 26 arranged to rotate the horizontal member about a horizontal axis. A sliding member 28 is slidably mounted on the horizontal member 24 such that the sliding member 28 may move horizontally with respect to the horizontal member 24. In operation the horizontal axis of the horizontal member 24 is arranged coaxial with the axis X of the inlet, or outlet, nozzle 12.

An arcuate member 30 is supported from the sliding member 28, and the arcuate member 30 has a frame 32 to which a wheel 34 is rotatably mounted. The arcuate member 30 also has a pair of arcuate tracks 36. A carriage 38 is mounted on the arcuate member 30 by means of rollers 40, which are arranged to run on the arcuate tracks 36, so that the carriage 38 may be moved through an arc of a circle. The carriage 38 has a motor 47 arranged to drive the carriage 38 along the arcuate tracks 36. The arcuate member 30 is biased outwardly towards the pressure vessel 10 to maintain the axis of the arcuate member 30 and arcuate tracks 36 coaxial with the axis 18 of curvature of the corner, or bend, 14 at that particular angular position. The arcuate member is biased by any suitable means, for example a spring. The biasing of the arcuate member 30 radially outwardly to the correct position is achieved when the wheel 34 abuts against the interior surface of the pressure vessel 10.

Figure 3:
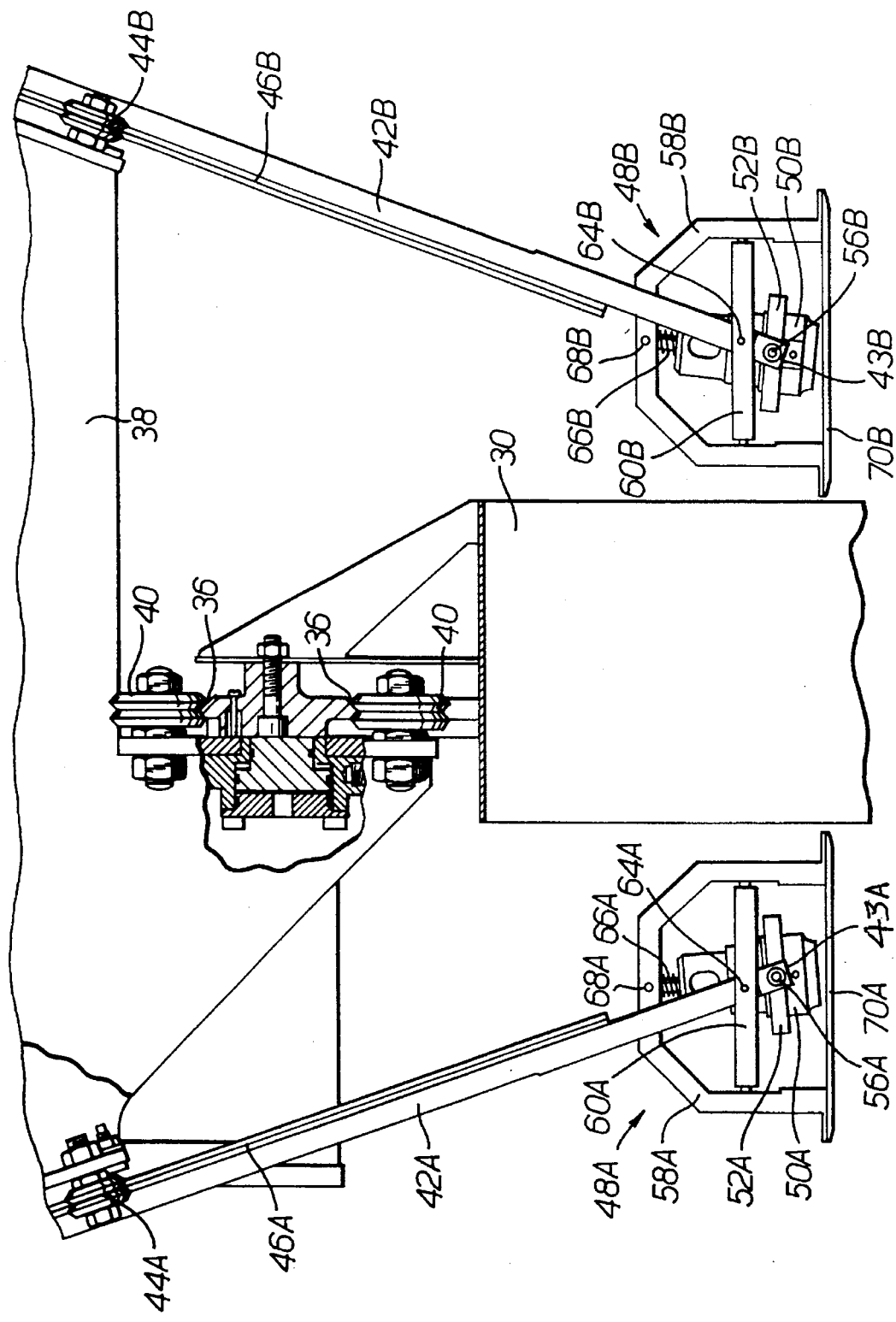
FIG. 3 is a cross-sectional view to an enlarged scale in the direction of arrows A—A in FIG. 2.
Figure 4:
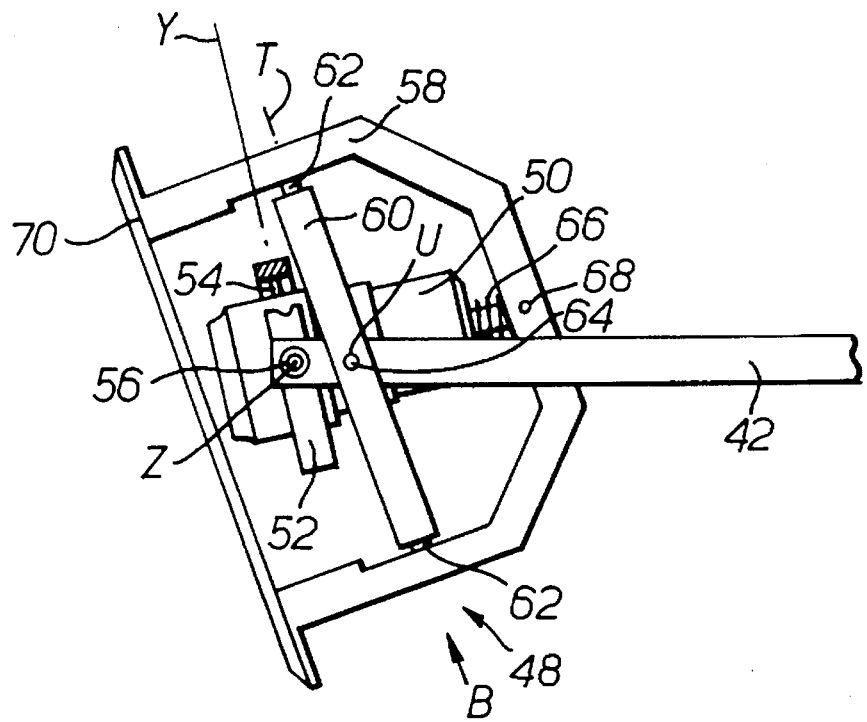
FIG. 4 is a further enlarged view of a gimbal arrangement of one probe assembly.
Figure 5:
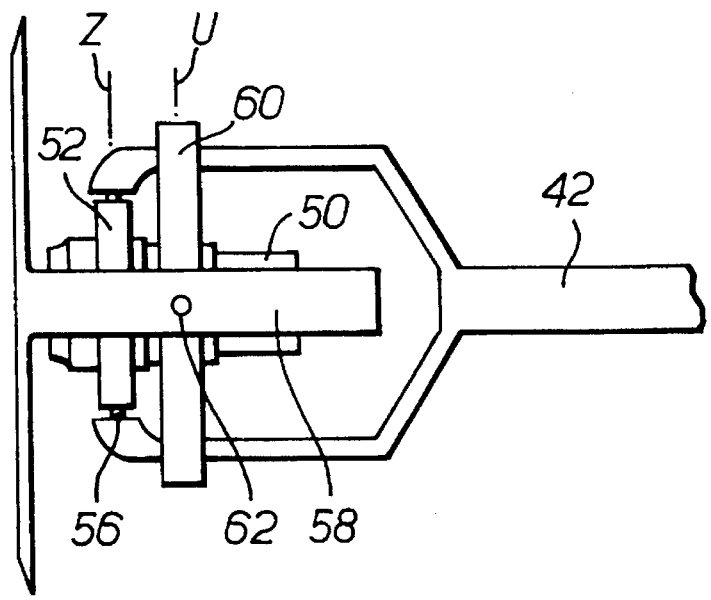
FIG. 5 is a view in the direction of arrow B in FIG. 4.

The carriage 38 carries a pair of elongate members 42A and 42B which are biased to move radially outwardly towards the interconnection between the pressure vessel 10 and the inlet, or outlet, nozzle 12. The elongate members 42A and 42B are biased by any suitable means, for example by springs. The elongate members 42A and 42B have tracks 46A and 46B respectively which cooperate with rollers 44A and 44B respectively on the carriage 38 to mount the elongate members 4 2A and 42B on the carriage 38. The tracks 46A and 46B and rollers 44A and 44B allows the elongate members 42A and 42B to move relative to the carriage 38. The elongate members 4 2A and 42B are arranged in a common plane at any suitable fixed predetermined angle for time of flight inspection. The predetermined angle shown in FIG. 3 is 40°, ideally the predetermined angle is 60°.

A first probe assembly 48A is mounted a first end 43A of the first elongate member 42A and a second probe assembly 48B is mounted on a first end 43B of the second elongate member 42B.

The first probe assembly 48A comprises a first ultrasonic probe 50A which is pivotally mounted onto a first ring member 52A about a first axis Y by spindles 54. The first ring member 52A is pivotally mounted to the first end 43A of the first elongate member 42A about a second axis Z by spindles 56. The first and second axes Y and Z are mutually perpendicular and the axes are in a common plane. A second member, a yoke, 58A is pivotally mounted to a third ring member 60A about a third axis T by spindles 62. The third ring member 60A is pivotally mounted to the first end 43A of the first elongate member 42A about a fourth axis U by spindles 64. The third and fourth axes T and U are mutually perpendicular and are arranged in a common plane. The second and fourth axes Z and U respectively are parallel but are spaced apart longitudinally of the elongate member 4 2A. The first axis Z is nearest to the first end 43A of the first elongate member 42A. It can be seen that the first ultrasonic probe 50A is gimballed to the first end 43A of the first elongate member 42A. The second member 58A carries a flat circular member 70A which in operation is arranged to contact the interior surface of the pressure vessel 10 and inlet, or outlet, nozzle 12.0 The position of the first ultrasonic probe 50A is controlled by the second member 58A by interaction therebetween by a spring 66A such that the axis of the first ultrasonic probe 50A passes through the imaginary point 68A on the second member 58A.

The second probe assembly 48B comprises a second ultrasonic probe 50B which is pivotally mounted onto a fourth ring member 52B about a fifth axis Y by spindles 54B. The fourth ring member 52B is pivotally mounted to the first end 43B of the second elongate member 4 2B about a sixth axis Z by spindles 56. The fifth and sixth axes Y and Z are mutually perpendicular and the axes are in a common plane. A fifth member, a yoke, 58B is pivotally mounted to a sixth ring member 60B about a seventh axis T by spindles 62. The sixth ring member 60B is pivotally mounted to the first end 43B of the second elongate member 42B about an eighth axis U by spindles 64. The seventh and eighth axes T and U are mutually perpendicular and are arranged in a common plane. The sixth and eighth axes Z and U respectively are parallel but are spaced apart longitudinally of the elongate member 42B. The fifth axis Z is nearest to the first end 43B of the second elongate member 42B. It can be seen that the second ultrasonic probe 50B is gimballed to the first end 43B of the second elongate member 42B. The fifth member 58B carries a flat circular member 70B which in operation is arranged to contact the interior surface of the pressure vessel 10 and inlet, or outlet, nozzle 12. The position of the second ultrasonic probe 50B is controlled by the fifth member 58B by interaction therebetween by a spring 66A such that the axis of the second ultrasonic probe 50B passes through the imaginary point 68B on the fifth member 58B.

The first ultrasonic probe 50A is gimballed onto the first elongate member 42A and the first yoke 58A is gimballed onto the first elongate member 42A. The second ultrasonic probe 50B is gimbal led onto the second elongate member 42B and the second yoke 58B is gimballed onto the second elongate member 4 2B.

The ratio of the distance between the imaginary point 68A,68B and the axis Z of rotation of the rings 52A,52B about the elongate members 42A,42B and the distance between the imaginary point 68A,68B and the axis U of rotation of the rings 60 about the elongate members 42A, 42B is selected according to the material of the object to be inspected in order to ensure that the ultrasonic beams in the material of the object are parallel with the longitudinal direction of the elongate members.

In operation the first ultrasonic probe 50A transmits an ultrasonic beam which passes through water within the nuclear reactor pressure vessel 10. The ultrasonic beam then passes through the interface between the water and the pressure vessel 10 and the ultrasonic beam is bent as is passes through the interface. The arrangement of the inspection apparatus 20 is such that the ultrasonic beam then travels through the material of the pressure vessel in a direction parallel to the longitudinal direction of the first elongate member 42A. The ultrasonic beam is focused at the exterior surface of the corner, or bend, 14. Reflected ultrasonic signals travel back towards the inspection apparatus 20. The second ultrasonic probe 50B is arranged to detect ultrasonic signals travelling in a direction parallel to the longitudinal direction of the second elongate member 42B. Again the reflected ultrasonic beam is bent as it passes through the interface. Any defects, for example cracks, in the corner 14 such as in the weld joint between the pressure vessel 10 and the inlet nozzle 12 are detected.

To inspect the whole of the corner 14 the motor 47 is actuated so that the carriage 38 moves along the arcuate member 30 so that the ultrasonic beam scans the exterior surface of the corner 14 in one radial direction relative to the ax s X of the inlet nozzle 12. The motor 26 is actuated to rotate the horizontal member 24 about the axis X of the inlet nozzle 12 through 360°. This causes the ultrasonic beam to scan the exterior surface of the corner 14 in a circumferential direction. Therefore the motor 47 moves the inspection apparatus 20 through small angles in a stepwise manner such that at each angular position the carriage 38 moves along the arcuate member 30 such that the corner 14 is ultrasonically scanned at each angular position.

It is to be noted that as the motor 47 rotates the inspection apparatus around the axis X of the inlet nozzle 12 the biasing means ensures that the axis of the arcuate member 30 and tracks 36 is maintained coaxial with the axis 18 of the corner 14 at that particular angular position. The probe assemblies take into account the refraction of the ultrasound at the interface between the water and the pressure vessel so that the ultrasonic beam is parallel to the longitudinal direction of the elongate members 42A,42B. The elongate members 42A and 42B are biased such that the flat circular members 70A,70B contact the interior surface of the pressure vessel 10 and/or inlet nozzle 12 to follow the profile of the interior surface.

The present invention minimises the number of ultrasonic probes and scanning time required for the exterior surface of the corner formed between the pressure vessel and the inlet nozzle. It ensures that irrespective of the scanning surface the ultrasonic beam from each ultrasonic probe intersects at the outer blend radius at a common azimuthal point. It controls the attitude of the ultrasonic probes such that when viewed in and axial/radial slice the ultrasonic beams intersect the blend radius normally i.e. if the midpoint of a line drawn between the two ultrasonic probes is projected to the blend radius then it will be normal to the radius at that point in the radial/axial plane only. It automatically varies the ultrasonic probe separation to compensate for varying wall thickness. It maintains the alignment of the ultrasonic beams such that the point of intersection does not vary.

I claim:

1. An apparatus for detecting defects in a wall of a hollow object, the object having a contoured exterior surface, the apparatus comprising a first ultrasonic probe pivotally mounted to a first member about a first axis, the first member is pivotally mounted to a first elongate member about a second axis, the first and second axes are mutually perpendicular and are arranged in a first plane, a second member pivotally mounted to a third member about a third axis, the third member is pivotally mounted to the first elongate member about a fourth axis, the third and fourth axes are mutually perpendicular and are arranged in a second plane, the second and fourth axes are spaced apart and are parallel, the second member is arranged to act on the first ultrasonic probe such that in operation the first ultrasonic probe transmits ultrasound into the object in a plane parallel to the first elongate member, a second ultrasonic probe pivotally mounted to a fourth member about a fifth axis, the fourth member is pivotally mounted to a second elongate member about a sixth axis, the fifth and sixth axes are mutually perpendicular and are arranged in a third plane, a fifth member pivotally mounted to a sixth member about a seventh axis, the sixth member is pivotally mounted to the second elongate member about an eighth axis, the seventh and eighth axes are mutually perpendicular and are arranged in a fourth plane, the sixth and eighth axes are spaced apart and are parallel, the fifth member is arranged to act on the second ultrasonic probe such that in operation the second ultrasonic probe receives ultrasound travelling in the object in a plane parallel to the second elongate member, the first and second elongate members are arranged at a predetermined angle such that the first ultrasonic probe and second ultrasonic probe are focused at a common point on the contoured exterior surface of the object.

2. An apparatus as claimed in claim 1 in which the first member is a ring.

3. An apparatus as claimed in claim 1 in which the third member is a ring.

4. An apparatus as claimed in claim 1 in which the first ultrasonic probe has a spring which abuts against the second member.

5. An apparatus as claimed in claim 1 in which the fourth member is a ring.

6. An apparatus as claimed in claim 1 in which the sixth member is a ring.

7. An apparatus as claimed in claim 1 in which the second ultrasonic probe has a spring which abuts against the fifth member.

8. An apparatus as claimed in claim 1 in which the first and second elongate members are mounted on a carriage, the first elongate member is movable relative to the carriage in the longitudinal direction of the first elongate member, the second elongate member is movable relative to the carriage in the longitudinal direction of the second elongate member.

9. An apparatus as claimed in claim 8 in which said first and second elongate members are biased by biasing means to move in the direction towards the ultrasonic probes.

10. An apparatus as claimed in claim 9 in which the biasing means are springs.

11. An apparatus as claimed in claim 8 in which the carriage is mounted on an arcuate track and the carriage moves along the arcuate track.

12. An apparatus as claimed in claim 11 in which the arcuate track is rotatably mounted on a support member.

13. An apparatus as claimed in claim 12 in which the support member comprises a vertical support member and a horizontal support means.

14. An apparatus as claimed in claim 11 in which the elongate members are biased to moved radially relative to the axis of the arcuate track member.

15. An apparatus as claimed in claim 14 in which the horizontal support means is rotatably mounted on the vertical support member about a horizontal axis, the arcuate track member is supported by the horizontal support means.

16. An apparatus as claimed in claim 15 in which the horizontal support means comprises a horizontal member rotatably mounted on the vertical support member and a sliding member slidably mounted on the horizontal member, the arcuate track member is supported by the sliding member.

17. An apparatus as claimed in claim 1 in which the second member comprises a member which is arranged to contact the interior surface of the hollow object.

18. An apparatus as claimed in claim 17 in which the fifth member comprises a member which is arranged to contact the interior surface of the hollow object.

19. An apparatus for detecting defects in a wall of a hollow object, the object having a contoured exterior surface, the apparatus comprising a first ultrasonic probe pivotally mounted to a first member about a first axis, the first member is pivotally mounted to a first elongate member about a second axis, the first and second axes are mutually perpendicular and are arranged in a first plane, a second member pivotally mounted to a third member about a third axis, the third member is pivotally mounted to the first elongate member about a fourth axis, the third and fourth axes are mutually perpendicular and are arranged in a second plane, the second and fourth axes are spaced apart and are parallel, the second member is arranged to act on the first ultrasonic probe such that in operation the first ultrasonic probe transmits ultrasound into the object in a plane parallel to the first elongate member.

20. An apparatus as claimed in claim 19 in which the first member is a ring.

21. An apparatus as claimed in claim 19 in which the third member is a ring.

22. An apparatus as claimed in claim 19 in which the first ultrasonic probe has a spring which abuts against the second member.

* * * * *